US00PP15530P2

(12) United States Plant Patent
Heuger

(10) Patent No.: US PP15,530 P2
(45) Date of Patent: Feb. 1, 2005

(54) ***HELLEBORUS* PLANT NAMED 'HGC DOUBLE SURPRISE'**

(50) Latin Name: *Helleborus orientalis*
Varietal Denomination: HGC Double Surprise

(76) Inventor: Joseph Heuger, Müsterstrasse 49, 49129 Glandorf (DE)

( * ) Notice: Subject to any disclaimer, the term of this patent is extended or adjusted under 35 U.S.C. 154(b) by 0 days.

(21) Appl. No.: 10/878,418

(22) Filed: Jun. 28, 2004

(51) Int. Cl.[7] ..... A01H 5/00
(52) U.S. Cl. ..... Plt./263
(58) Field of Search ..... Plt./263

(56) References Cited

PUBLICATIONS

UPOV ROM GTITM Computer Datbase, GTI JOUVE Retrieval Software 2004/40 Citation(s) for 'Double Surprise'.*

Huxley, Anthony, ed. RHS Dictionary of Gardening, vol. 2 D–K. New York: The Stockton Press: 1992. pp. 538–542.*

Wayside Gardens Autumn Catalog 1999; cover, last page and p. 72.*

Seyring, M. In vitro cloning of *Helleborus niger*. Plant Cell Reports 20 (10): p 895–900 Mar. 2002 (abstract).*

Sunset National Garden Book Mar. 1997, Sunset Books, Menlo Park CA, p. 331.*

* cited by examiner

*Primary Examiner*—Kent Bell
*Assistant Examiner*—W C Haas
(74) *Attorney, Agent, or Firm*—C. A. Whealy

(57) ABSTRACT

A new and distinct cultivar of *Helleborus* plant named 'HGC Double Surprise', characterized by its upright plant habit; dark green-colored leaves; typically more than one flowering stem per plant; attractive double white-colored flowers with purple-colored spots; and long flowering period.

1 Drawing Sheet

Botanical classification/cultivar designation: *Helleborus orientalis* Hybrid cultivar HGC Double Surprise.

BACKGROUND OF THE INVENTION

The present Invention relates to a new and distinct cultivar of *Helleborus* plant, botanically known as *Helleborus orientalis* Hybrid, and hereinafter referred to by the cultivar name HGC Double Surprise.

The new *Helleborus* is a product of a planned breeding program conducted by the Inventor in Glandorf, Germany. The objective of the breeding program was to create new *Helleborus* cultivars with a good plant habit, that flower for a long period of time, and have attractive flower coloration.

The new *Helleborus* originated from a cross-pollination made by the Inventor in January, 1999 in Glandorf, Germany of an unnamed seedling of *Helleborus orientalis* Hybrid, not patented, as the female, or seed, parent with an unnamed seedling of *Helleborus orientalis* Hybrid, not patented, as the male, or pollen, parent. The new *Helleborus* was discovered and selected by the Inventor as a flowering plant within the progeny of the stated cross-pollination in a controlled environment in Glandorf, Germany.

Asexual reproduction of the new cultivar by divisions at Glandorf, Germany since March, 2001, has shown that the unique features of this new *Helleborus* are stable and reproduced true to type in successive generations.

SUMMARY OF THE INVENTION

Plants of the cultivar HGC Double Surprise have not been observed under all possible environmental conditions. The phenotype may vary somewhat with variations in environment such as temperature and light level without, however, any variance in genotype.

The following traits have been repeatedly observed and are determined to be the unique characteristics of 'HGC Double Surprise'. These characteristics in combination distinguish 'HGC Double Surprise' as a new and distinct cultivar of *Helleborus:*

1. Upright plant habit.
2. Dark green-colored leaves.
3. Typically more than one flowering stem per plant.
4. Attractive double white-colored flowers with purple-colored spots.
5. Long flowering period.

Plants of the new *Helleborus* differed from plants of the parent selections primarily in flower form.

Plants of the new *Helleborus* can be compared to the *Helleborus niger* cultivar HGC Jericho, disclosed in U.S. Plant patent application Ser. No. 10/878,420. In side-by-side comparisons conducted in Glandorf, Germany, plants of the new *Helleborus* differed from plants of the cultivar HGC Jericho in the following characteristics:

1. Plants of the new *Helleborus* were taller than plants of the cultivar HGC Jericho.
2. Plants of the new *Helleborus* had longer leaf petioles than plants of the cultivar HGC Jericho.
3. Plants of the new *Helleborus* had double flowers whereas plants of the cultivar HGC Jericho had single flowers.
4. Plants of the new *Helleborus* had smaller flowers than plants of the cultivar HGC Jericho.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Helleborus*.

The photograph at the top of the sheet comprises a side perspective view of a typical flowering plant of 'HGC Double Surprise'.

The photograph at the bottom of the sheet is a close-up view of a typical flower of 'HGC Double Surprise'.

DETAILED BOTANICAL DESCRIPTION

The aforementioned photographs, following observations and measurements describe plants grown in Glandorf, Germany, in a glass-covered greenhouse and under commercial production practices during the winter. Plants were grown in 15-cm containers and were about six months old when the photographs and description were taken. During the production of the plants, day temperatures were about 18° C. and night temperatures were about 14° C. In the following description, color references are made to The Royal Horticultural Society Colour Chart, 1995 Edition, except where general terms of ordinary dictionary significance are used.

Botanical classification: *Helleborus orientalis* Hybrid cultivar HGC Double Surprise.

Parentage:

*Female parent.*—Unnamed seedling of *Helleborus orientalis* Hybrid, not patented.

*Male parent.*—Unnamed seedling of *Helleborus orientalis* Hybrid, not patented.

Propagation:

*Type.*—By divisions.

*Time to initiate roots, winter.*—About eight weeks at 12° C.

*Time to produce a rooted plant, winter.*—About six months at 12 to 15° C.

*Root description.*—About 3 to 15 thick fleshy roots; not branching; white to brown in color.

Plant description:

*Plant form/habit.*—Upright plant habit; inverted triangle; vigorous growth habit. Leaves basal with upright peduncles. Double flower form.

*Plant height.*—About 42 cm.

*Plant width* (*spread*).—About 30 cm.

*Foliage description.*—Arrangement: Basal; palmately compound with five to seven leaflets per leaf. Leaflet length: About 4 to 13 cm. Leaflet width: About 1.2 to 5.5 cm. Leaflet shape: Lanceolate; pedate. Leaflet apex: Acute. Leaflet base: Acute. Leaflet margin: Serrate. Texture, upper and lower surfaces: Smooth, glabrous. Venation pattern: Reticulate. Color: Developing leaflets, upper surface: Closest to 144A. Developing leaflets, lower surface: 146C. Fully expanded leaflets, upper surface: Closest to 137A. Fully expanded leaflets, lower surface: Closest to 147B. Venation, upper surface: 146D. Venation, lower surface: 146C. Petiole: Length: About 10 to 17 cm. Diameter: About 3 to 5 mm. Texture, upper and lower surfaces: Smooth, glabrous. Color, upper and lower surfaces: 144A overlain with 187C.

Flower description:

*Flower type/habit.*—Double rounded flowers arranged in terminal cymes; petals inconspicuous; flowers somewhat weeping; typically more than one flowering stem per plant. Freely flowering habit with about 15 flowers developing per plant over the flowering period.

*Fragrance.*—None detected.

*Natural flowering season.*—Long flowering period; intermittent flowering from January through March in Glandorf, Germany. Flowers persistent.

*Postproduction longevity.*—Flowers last about ten days on the plant.

*Flower buds.*—Height: About 1.7 cm. Diameter: About 1.2 cm. Shape: Ovoid. Color: 145C.

*Flowers.*—Diameter: About 5 cm. Depth: About 3 cm.

*Petals.*—Size: Minute, obscured by reproductive organs; forming inconspicuous nectaries.

*Sepals.*—Quantity/arrangement per flower: Typically 17 to 20 in three whorls. Length: About 3.5 cm. Width: About 3 cm. Shape: Broadly ovate. Apex: Broadly acute. Margin: Entire. Texture, upper and lower surfaces: Smooth, glabrous; satiny. Color: Developing sepals, upper surface: 155A with spots towards the center, 187C. Developing sepals, lower surface: 155A; towards the base, 145A. Fully expanded sepals, upper surface: 155A with spots towards the center, 187C; towards the base, 145A. Color becoming closer to 145C with development. Fully expanded sepals, lower surface: Between 145D and 155A; towards the base, 145A.

*Peduncles.*—Length: About 20 to 30 cm. Diameter: About 5 to 8 mm. Orientation: Upright. Strength: Strong, but bend slightly with the weight of the flowers. Texture: Smooth, glabrous. Color: 146B overlain with 187C.

*Pedicels.*—Length: About 4 to 15 cm. Diameter: About 3 to 5 mm. Orientation: Upright. Strength: Strong, but bend slightly with the weight of the flowers. Texture: Smooth, glabrous. Color: 145C.

*Reproductive organs.*—Stamens: Quantity per flower: About 30. Anther shape: Oblong. Anther length: About 3 mm. Anther color: 145D. Pollen amount: None observed. Pistils: Quantity per flower: About six. Pistil length: About 1.2 cm. Stigma shape: Tuberculate. Stigma color: 145D. Style length: About 1 cm. Style color: 145B. Ovary color: 145B.

*Seed/fruit.*—Seed and fruit development have not been observed.

Disease/pest resistance: Plants of the new *Helleborus* have not been noted to be resistant to pathogens and pests common to *Helleborus*.

Temperature tolerance: Plants of the new *Helleborus* have been observed to tolerate temperatures from −12 to 36° C.

It is claimed:

1. A new and distinct cultivar of *Helleborus* plant named 'HGC Double Surprise', as illustrated and described.

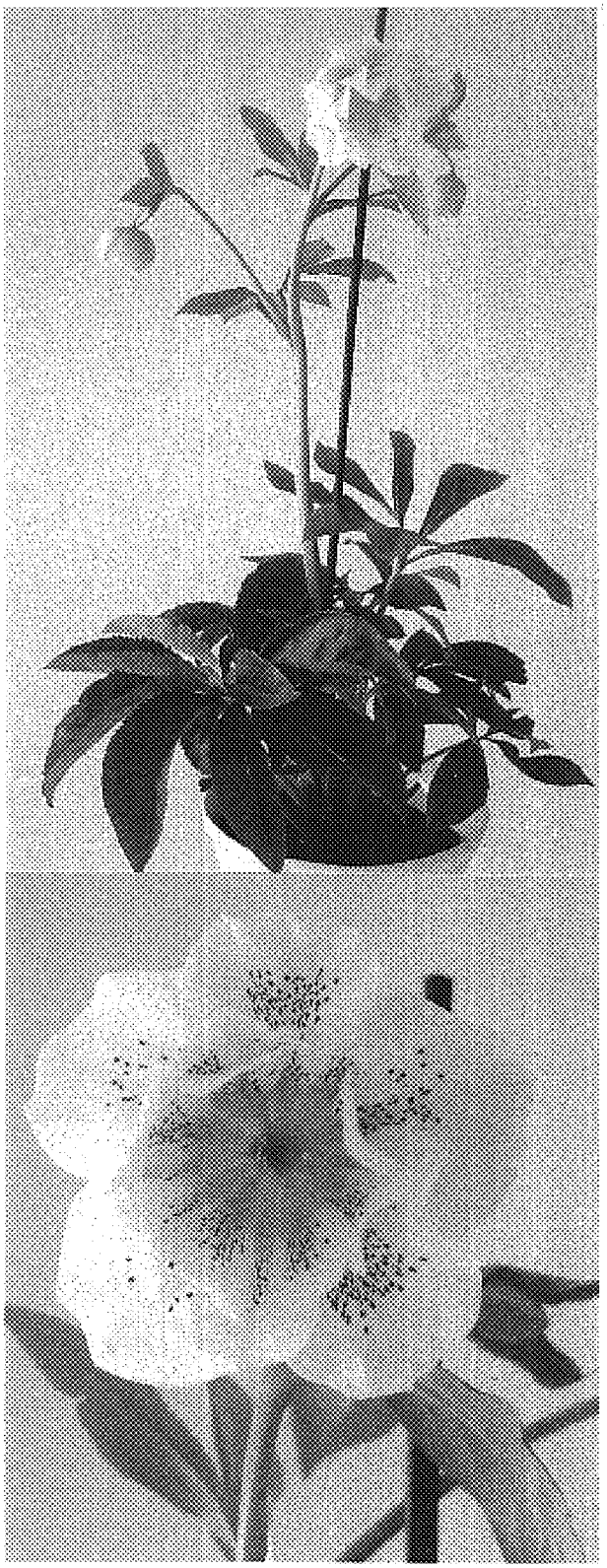

* * * * *